(12) United States Patent
Isaacson et al.

(10) Patent No.: US 10,850,046 B2
(45) Date of Patent: Dec. 1, 2020

(54) CANNULA LOCATOR DEVICE (71) Applicant: Becton, Dickinson and Company, Franklin Lakes, NJ (US)

(72) Inventors: S. Ray Isaacson, Layton, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 489 days.

(21) Appl. No.: 15/461,367

(22) Filed: Mar. 16, 2017

(65) Prior Publication Data

US 2017/0274156 A1 Sep. 28, 2017

Related U.S. Application Data (60) Provisional application No. 62/314,269, filed on Mar. 28, 2016.

(51) Int. Cl.
*A61B 90/11* (2016.01)
*A61M 5/42* (2006.01)
(Continued)

(52) U.S. Cl.
CPC ............ *A61M 5/427* (2013.01); *A61B 1/042* (2013.01); *A61B 1/05* (2013.01); *A61B 1/07* (2013.01); *A61B 90/11* (2016.02); *A61M 25/0618* (2013.01); *A61M 25/0693* (2013.01); *A61B 2017/00061* (2013.01);
(Continued)

(58) Field of Classification Search
None
See application file for complete search history.

(56) References Cited

U.S. PATENT DOCUMENTS 3,789,841 A 2/1974 Antoshkiw
4,317,445 A 3/1982 Robinson
(Continued)

FOREIGN PATENT DOCUMENTS

EP 2710974 3/2014
JP H05506949 10/1993
(Continued)

OTHER PUBLICATIONS

Schneider et al: "The Fibre Fabry Perot sensor. A long-term manometry sensor for quantitative intraluminal pressure measurement of the gastrointestinal tract", Clinical Physics and Physiological Measurement, Institute of Physics Publishing, Bristol, GB, vol. 11, No. 4, Nov. 1, 1990, pp. 319-325.

*Primary Examiner* — Joanne M Hoffman
(74) *Attorney, Agent, or Firm* — Kirton & McConkie; Craig Metcalf; Kevin Stinger (57) ABSTRACT

A cannula locator device is described herein. The cannula locator device may include a cannula. The cannula may include a distal tip, an elongated tubular shaft, and an inner lumen formed by the elongated tubular shaft. The cannula locator device may also include a first optical fiber configured to emit light and a second optical fiber configured to receive reflected light. The first and second optical fibers may be disposed within the inner lumen of the cannula. The first optical fiber may include a first distal end and a first proximal end. The second optical fiber may include a first proximal end and first distal end.

20 Claims, 4 Drawing Sheets

(51) Int. Cl.
*A61B 1/04* (2006.01)
*A61B 1/05* (2006.01)
*A61B 1/07* (2006.01)
*A61M 25/06* (2006.01)
*A61B 17/00* (2006.01)
*A61B 90/30* (2016.01)
*A61B 34/20* (2016.01)
*A61B 90/00* (2016.01)

(52) U.S. Cl.
CPC ........... *A61B 2017/00115* (2013.01); *A61B 2034/2055* (2016.02); *A61B 2090/306* (2016.02); *A61B 2090/3614* (2016.02); *A61M 2205/18* (2013.01); *A61M 2205/584* (2013.01)

(56) References Cited

U.S. PATENT DOCUMENTS

| | | | |
|---|---|---|---|
| 4,682,895 A | 7/1987 | Costello | |
| 5,092,845 A * | 3/1992 | Chang | A61M 25/0631 604/168.01 |
| 5,124,130 A | 6/1992 | Costello et al. | |
| 5,452,076 A | 9/1995 | Schopper et al. | |
| 5,460,182 A | 10/1995 | Goodman et al. | |
| 5,772,636 A | 6/1998 | Brimhall et al. | |
| 7,496,392 B2 * | 2/2009 | Alarcon | G01N 21/7703 600/317 |
| 7,787,923 B2 | 8/2010 | Alarcon et al. | |
| 8,597,252 B2 | 12/2013 | Burkholz et al. | |
| 9,339,221 B1 * | 5/2016 | Heaton, II | A61B 5/1459 |
| 9,700,697 B2 | 7/2017 | Gasparyan et al. | |
| 9,737,213 B1 * | 8/2017 | Heaton, II | A61B 17/122 |
| 2006/0167405 A1 | 7/2006 | Kint et al. | |
| 2006/0184048 A1 * | 8/2006 | Saadat | A61B 1/0008 600/478 |
| 2006/0264745 A1 * | 11/2006 | Da Silva | A61B 5/0084 600/434 |
| 2007/0016130 A1 * | 1/2007 | Leeflang | A61B 1/00165 604/95.04 |
| 2007/0293748 A1 | 12/2007 | Engvall et al. | |
| 2008/0009751 A1 * | 1/2008 | Berndt | A61B 5/0075 600/478 |
| 2008/0243031 A1 * | 10/2008 | Seibel | A61B 1/0008 600/566 |
| 2008/0249487 A1 | 10/2008 | Engvall | |
| 2008/0262359 A1 * | 10/2008 | Tearney | A61B 1/00096 600/476 |
| 2010/0081873 A1 * | 4/2010 | Tanimura | A61B 1/00096 600/109 |
| 2010/0317964 A1 * | 12/2010 | Hendriks | A61B 5/0075 600/424 |
| 2011/0009772 A1 | 1/2011 | Braun et al. | |
| 2011/0077477 A1 | 3/2011 | Romey et al. | |
| 2011/0255828 A1 | 10/2011 | Sudarshanam | |
| 2012/0088991 A1 * | 4/2012 | Nachabe | G16H 40/63 600/310 |
| 2012/0215065 A1 * | 8/2012 | Mukherjee | A61B 1/042 600/108 |
| 2014/0276024 A1 | 9/2014 | Stigall et al. | |
| 2015/0305603 A1 * | 10/2015 | Gal | A61B 1/00167 600/103 |
| 2015/0314105 A1 * | 11/2015 | Gasparyan | A61M 5/427 604/510 |
| 2017/0274184 A1 * | 9/2017 | Isaacson | A61M 25/0067 |
| 2017/0281287 A1 * | 10/2017 | Au | A61M 25/0113 |

FOREIGN PATENT DOCUMENTS

| | | |
|---|---|---|
| JP | H0829207 | 2/1996 |
| JP | H08131549 | 5/1996 |
| JP | 2010523197 | 7/2010 |
| JP | 2013009949 | 1/2013 |
| JP | 2013502269 | 1/2013 |
| JP | 2013542773 | 11/2013 |
| KR | 20180135257 | 12/2018 |
| WO | 86/03832 | 7/1986 |
| WO | 2006/001759 | 1/2006 |
| WO | 2009/123026 | 10/2009 |
| WO | 2012/101583 | 8/2012 |
| WO | 2012/101584 | 8/2012 |
| WO | 2015/056257 | 4/2015 |
| WO | 2015/168655 | 11/2015 |
| WO | 2015/200712 | 12/2015 |

* cited by examiner

CANNULA LOCATOR DEVICE

RELATED APPLICATIONS

This application claims the benefit of U.S. Provisional Patent Application No.: 62/314,269, filed on Mar. 28, 2016, and entitled CANNULA LOCATOR DEVICE, which is incorporated herein in its entirety.

BACKGROUND OF THE INVENTION

This disclosure relates generally to cannula locator devices, systems, and associated methods.

Placing a cannula in a desired destination of a body of a patient may be a difficult task for a clinician in the medical field. For example, it may be difficult to place the cannula in proper position in a blood vessel, such as a vein, for infusion and/or blood collection. It may also be difficult to place the cannula in proper position in a spinal canal for infusion and/or cerebrospinal fluid collection. The clinician may want to advance the cannula far enough to access the blood or cerebrospinal fluid but may not want to advance the cannula too far so as to injure a wall of the vein, the spinal cord, or the spinal cord dura. Thus, it is important for the clinician to know when the cannula is located within the vein or spinal canal.

To assist in positioning the cannula in the vein to be accessed, clinicians have traditionally used a number of techniques. These include use of a tourniquet, palpitation, rubbing the area, asking the patient to make a fist, and others. In some instances, to assist in positioning the cannula of a catheter device in the vein, the clinician may confirm that there is "flashback" of blood into, for example, a flashback chamber associated with the catheter device. Flashback generally entails an appearance of a small amount of blood within the catheter device, which may be visible to the clinician.

Once proper placement of a distal tip of the cannula into the blood vessel is confirmed via flashback, the clinician may apply pressure to the blood vessel by pressing down on the patient's skin over the blood vessel, distal to the cannula. The finger pressure may momentarily occlude the vessel, minimizing further blood flow through the cannula and the catheter device. The clinician may then withdraw the cannula from the catheter device. Flashback of blood into the flashback chamber may occur when the cannula is properly placed within the blood vessel but may be irreversible and may not provide a continuous indication that the cannula is properly placed. Further, flashback of blood into the flashback chamber may not be instantaneous, instead taking some time.

Accordingly, there is a need in the art for devices, systems, and methods that provide a continuous and/or instantaneous indication of a location of the distal tip of the cannula. Such devices, systems, and methods are disclosed herein.

BRIEF SUMMARY OF THE INVENTION

The present application relates generally to a cannula locator device. The cannula locator device may include a cannula, which may include a distal tip, an elongated tubular shaft, and an inner lumen formed by the elongated tubular shaft. In some embodiments, one or more optical fibers may be disposed within the inner lumen of the cannula. In some embodiments, one or more of the optical fibers may be configured to emit light, and one or more of the optical fibers may be configured to receive light reflected from an environment of the distal tip of the cannula (which may be referred to in the present disclosure as "reflected light"). In some embodiments, a single fiber may emit the light and receive the reflected light.

In some embodiments, each of the optical fibers may include a distal end and a proximal end. Each of the optical fibers configured to emit light (which may be referred to in the present disclosure as "emitting optical fibers") may emit light from their corresponding distal end, which may be disposed at least proximate the distal tip of the cannula. The light may be reflected by the environment of the distal tip of the cannula and received at distal ends of one or more optical fibers configured to receive the reflected light (which may be referred to in the present disclosure as "receiving optical fibers"). In some embodiments, the distal ends of the receiving optical fibers may be disposed at least proximate the distal end of the cannula.

In some embodiments, a large number of optical fibers may be disposed within the inner lumen, which may allow generation of an image of the environment of the distal tip of the cannula. For example, the proximal ends of the receiving optical fibers of the large number of optical fibers may be coupled with a camera, which may be configured to generate the image of the environment of the distal tip of the cannula from the reflected light. The camera may receive the reflected light from the proximal ends of the receiving optical fibers.

In other embodiments, a small number of optical fibers may be disposed within the inner lumen, which may allow simple, cost-effective detection of a color at the distal tip of the cannula. For example, one, two, or three optical fibers may be disposed within the inner lumen of the cannula. In these embodiments, a wavelength detector may be coupled with the proximal ends of the receiving optical fibers of the small number of optical fibers. In some embodiments, the wavelength detector may be configured to receive the reflected light, detect one or more wavelengths of the reflected light, and convert all or a portion of the reflected light into an electrical signal. In some embodiments, a signal processor may be coupled with the wavelength detector and may be configured to receive the electrical signal and determine a color of the reflected light.

In some embodiments, the color of the reflected light may correspond to a color of the environment of the distal tip of the cannula, the distal ends of the receiving optical fibers being at least proximate the distal tip of the cannula. The color of the environment of the distal tip of the cannula may indicate a location or position of the distal tip of the cannula, which may in turn indicate a location or position of a catheter coupled with the cannula. For example, a dark red color may indicate the distal tip of the cannula is located within a blood vessel of a patient. As another example, a particular color may indicate the distal tip of the cannula is located within cerebrospinal fluid in the spinal canal. Further, a change from one color to another may indicate movement of the distal tip of the cannula from one environment to another. For example, as the cannula is inserted into a blood vessel of the patient, the environment of the distal tip of the cannula may change from a white color as the distal tip moves through a wall of the blood vessel to a dark red color when the distal tip of the cannula is within the blood vessel. As another example, the environment of the distal tip of the cannula may change as the distal tip of the cannula proceeds through skin, fat, and tissue of the patient.

In some embodiments, the wavelength detector may be configured to detect a particular wavelength of the reflected light or range of wavelength of the reflected light, as will be explained later in further detail. In some embodiments, the signal processor may determine the color of the reflected light is a particular color, and in response to the determination that the color of the reflected light is a particular color, the signal processor may be further configured to initiate an alarm signal. For example, in response to the determination that the color of the reflected light is red or dark red, which may indicate the distal tip of the cannula is within the blood vessel of the patient, the signal processor may be configured to initiate an alarm signal, which may include an audible noise, a flashing light, etc. The alarm signal may indicate to a clinician that the distal tip of the cannula is located in a desired environment, such as, for example, within the blood vessel, within the cerebrospinal fluid, etc.

The cannula may comprise any cannula that can be used with the described location mechanism, including, but riot limited to, a hypodermic needle, such as an intravenous catheter (IV) introducer needle, a peripheral intravenous catheter (PIVC) introducer needle, an epidural introducer needle, a spinal tap needle, etc. In some embodiments, in addition to the cannula and the optical fibers, the cannula locator device may include a catheter adapter, which may include a catheter. In some embodiments, the cannula locator device may include a needle hub coupled with a proximal end of the cannula. In some embodiments, the needle hub may be selectively coupled with the catheter adapter. In some embodiments, the cannula locator device may include a flash chamber, which may be coupled with the needle hub. In some embodiments, the flash chamber may include a body and an air permeable membrane. An internal cavity of the body of the flash chamber may be in fluid communication with the inner lumen of the cannula.

In some embodiments, the cannula locator device may include a needle shield, which may be coupled with the catheter adapter. In some embodiments, all or a portion of the cannula and/or the optical fibers may be retracted into the needle shield for safety purposes and to prevent accidental needle sticks. For example, the distal tip of the cannula and/or the distal ends of the optical fibers may be retracted into the needle shield. In some embodiments, retraction of the distal tip of the cannula and/or the distal ends of the optical fibers may trap the distal tip and/or the distal ends within the needle shield. In some embodiments, the cannula and/or the optical fibers may be configured to move proximally within the needle shield after the catheter is inserted into a patient to thereby retract the distal tip and/or the distal ends of the optical fibers into the needle shield. In some embodiments, the cannula and/or the optical fibers may move proximally within the needle shield and/or an opening the proximal end of the needle sheild to thereby retract the distal tip and/or the distal ends within the needle shield.

In some embodiments, the flash chamber may be contained within the needle shield. In some embodiments, the optical fibers may extend through an opening in a proximal end of the needle shield. In some embodiments, the needle hub and/or the flash chamber may be configured to move proximally within the needle shield after the catheter is inserted into a patient to thereby retract the cannula and the distal ends of the optical fibers into the needle shield.

In some embodiments, the optical fibers may be spaced apart from an inner wall of the elongated tubular shaft, which may allow blood or another fluid to flow into the cannula and through a flash back notch in the cannula. It may be typical for the cannula to include a flashback notch towards its distal end. This flashback notch is oftentimes positioned within a catheter so that blood flowing out through the flashback notch will be visible within the catheter, which may provide visual confirmation of proper placement of the cannula and/or catheter within the blood vessel of the patient. When blood is seen flowing through the flashback notch, the clinician may know that the distal tip of the cannula is contained within a blood vessel.

In some embodiments, the optical fibers may act similar to a guidewire. For example, the one or more optical fibers may be configured to move past the distal tip of the cannula to guide a catheter into a patient. Typically, a guidewire may be made of metal and used to advance a catheter into the blood vessel of patient. The catheter may follow the guidewire into the blood vessel to reduce trauma to the blood vessel during advancement of the catheter into the blood vessel. In some embodiments, the optical fibers may not only reduce trauma to the blood vessel by guiding the catheter into the blood vessel, but may also illuminate the blood vessel, allowing the clinician to more clearly see a location of the blood vessel.

In some embodiments, the cannula locator device may include a light detector other than the optical fibers. In some embodiments, the light detector may be disposed within the inner lumen of the cannula. In some embodiments, the light detector may be disposed within the inner lumen of the cannula may include a camera coupled with one or more sheathed electrical cables. In some embodiments, the camera may be disposed at least proximate the distal tip of the cannula. In some embodiments, the sheathed electrical cables may extend through the inner lumen of the cannula. In some embodiments, the camera may be spaced apart from the inner wall of the elongated tubular shaft, which may allow blood to flow into the cannula and through a flash back notch in the cannula, as described above.

BRIEF DESCRIPTION OF THE SEVERAL VIEWS OF THE FIGURES

In order that the manner in which the above-recited and other features and advantages of the invention will be readily understood, a more particular description of the cannula capture mechanism briefly described above will be rendered by reference to specific embodiments thereof, which are illustrated in the appended Figures. Understanding that these Figures depict only typical embodiments and are not, therefore, to be considered to be limiting of its scope, the invention will be described and explained with additional specificity and detail through the use of the accompanying Figures in which.

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the Figures herein, could be arranged and designed in a wide variety of different configurations. Thus, the following more detailed description of the embodiments of the cannula locator device, cannula locator system, and associated methods, as represented in FIGS. 1 through 8, is not intended to limit the scope of the invention, as claimed, but is merely representative of some embodiments of the invention.

Generally, this application relates to a cannula locator device. In other words, this application discusses a cannula locator device that allows the distal tip of the cannula to be located using a light detector disposed with the cannula. Location of the distal tip of the cannula may allow a clinician to appropriately position the distal tip of the cannula during a medical procedure, such as, for example, an intravenous infusion, blood draw, spinal tap, or epidural.

Figure 1:
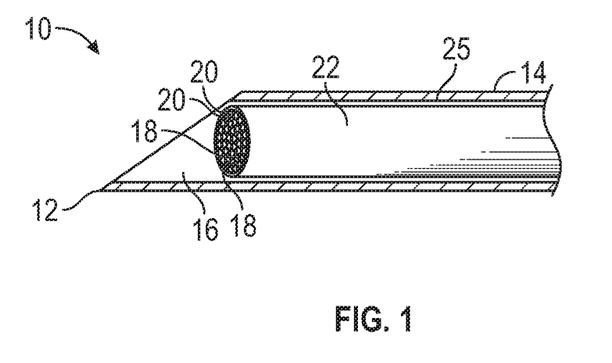
FIG. 1 is a cut-away side view illustrating an example optic fiber configuration disposed within an example cannula, according to some embodiments.
Figures 3, 4:
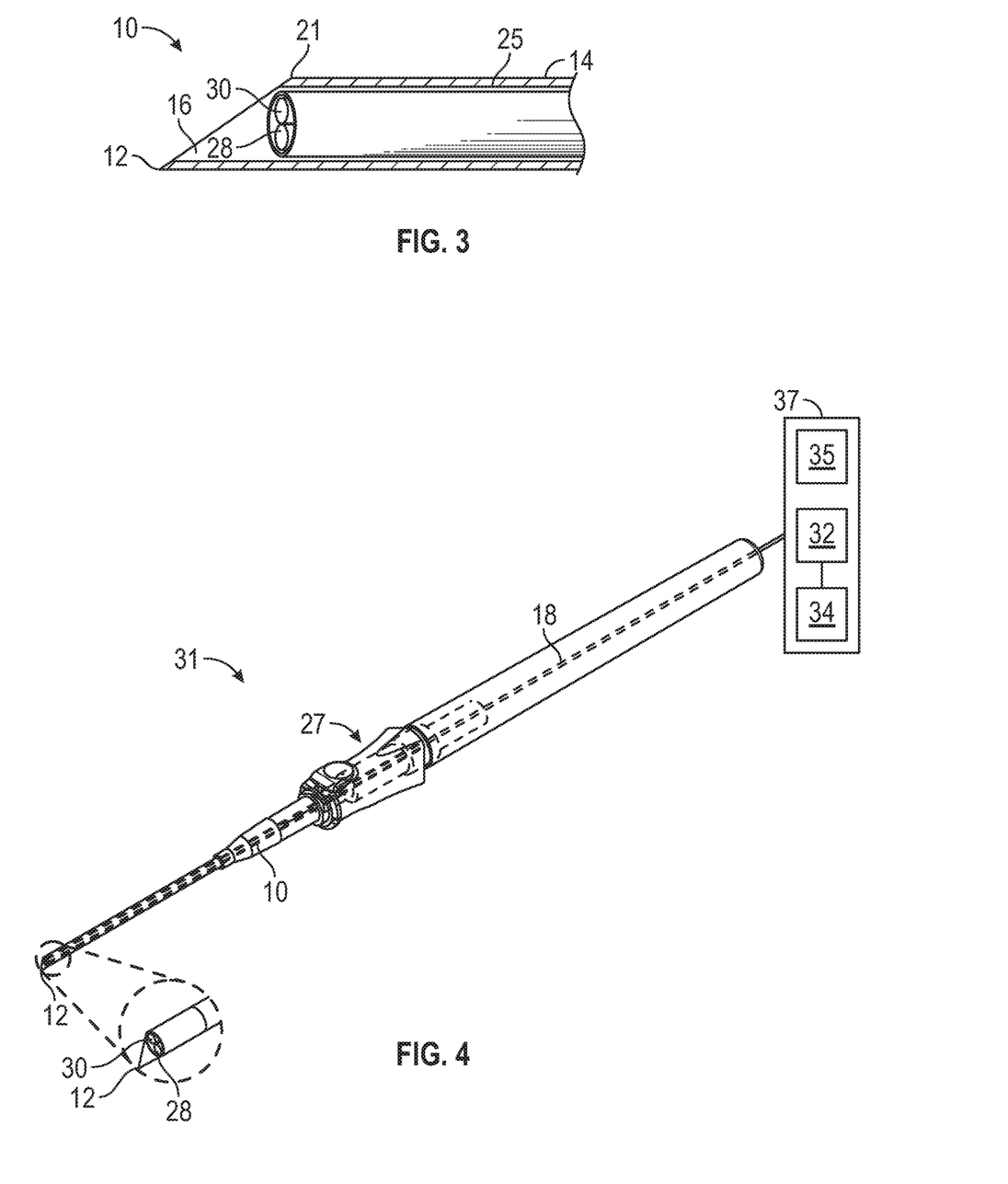
FIG. 3 is a cut-away side view illustrating another example optic fiber configuration disposed within the cannula, according to some embodiments.
FIG. 4 is a perspective view illustrating the cannula locator device of FIG. 2 in another cannula locator system, according to some embodiments.

Referring now to FIGS. 1 and 3, the cannula locator device may include a cannula 10, which may include a distal tip 12, an elongated tubular shaft 14, and an inner lumen 16 formed by the elongated tubular shaft 14. In some embodiments, one or more optical fibers 18 may be disposed within the inner lumen 16 of the cannula 10. In some embodiments, one or more of the optical fibers 18 may be configured to emit light, and one or more of the optical fibers 18 may be configured to receive light reflected from an environment of the distal tip 12 of the cannula 10 (which may be referred to in the present disclosure as "reflected light"). In some embodiments, a single optical fiber 18 may be disposed within the cannula 10. In some embodiments, one or more of the optical fibers 18 may emit the light and receive the reflected light.

In some embodiments, each of the optical fibers 18 may include a distal end 20 and a proximal end (not illustrated in FIG. 1). Each of the, optical fibers 18 configured to emit light (which may be referred to in the present disclosure as "emitting optical fibers") may emit light from a corresponding distal end 20, which may be disposed at least proximate the distal tip 12 of the cannula 10. The light may be reflected by an environment of the distal tip 12 of the cannula 10 and received at distal ends 20 of one or more of the optical fibers 18 configured to receive the reflected light (which may be referred to in the present disclosure as "receiving optical fibers"). In some embodiments, the distal ends 20 of the receiving optical fibers may also be disposed at least proximate the distal tip 12 of the cannula 10.

In some embodiments, each of the distal ends 20 of the optical fibers 18 may be disposed proximal to a beveled edge 21 of the distal tip 12, which may prevent the distal tip 21 from not being fully inserted into the blood vessel or spinal canal when the image is generated that indicates the distal tip 21 is properly placed or the color is detected that indicates the distal tip 21 is properly placed.

In some embodiments, the optical fibers 18 may be sheathed by a sheath 22 along a length of the optical fibers 18 between the distal ends 20 and the proximal ends 24. In some embodiments, the optical fibers 18 may be spaced apart from an inner wall 25 of the elongated tubular shaft 14, which may allow blood or another fluid to flow into the cannula and/or through a flash back notch in the cannula.

Figure 2:
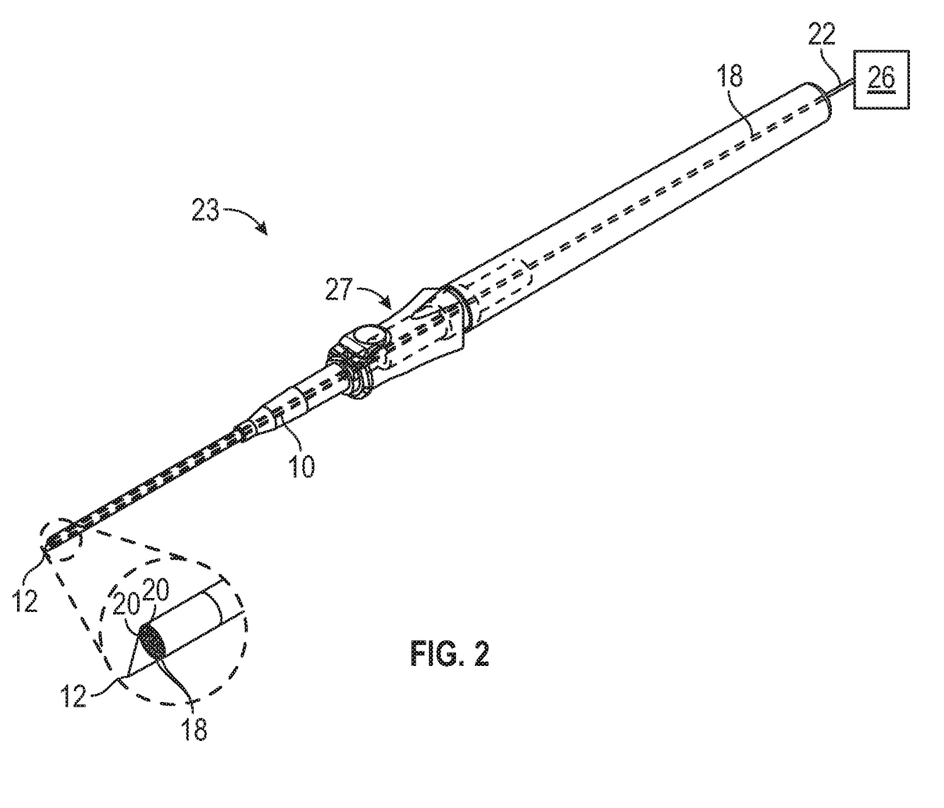
FIG. 2 is a perspective view illustrating an example cannula locator device in an example cannula locator system, according to some embodiments.

In some embodiments, as illustrated in FIG. 1, a large number of optical fibers 18 may be disposed within the inner lumen 16, which may allow generation of an image of the environment of the distal tip 12 of the cannula 10. For example, referring now to FIG. 2, illustrating the cannula locator device 27 in an example cannula locator system 23, the proximal ends 24 of the receiving optical fibers of the large number of optical fibers 18 may be coupled with a camera 26, which may be configured to generate an image of the environment of the distal tip 12 of the cannula 10 from the reflected light, which the camera 26 may receive from the proximal ends 24 of the receiving optical fibers.

The large number of optical fibers 18, illustrated in FIG. 1, may include any number of fibers, such as, for example, up to hundreds or thousands of optical fibers 18. In some embodiments, the optical fibers 18 may extend through all or a portion of a device, such as, for example, the cannula locator device 27, as will be explained further with respect to FIGS. 5A-5B. In some embodiments, the optical fibers 18 and surrounding sheath 22 may exit a proximal end of the cannula locator device 27. A position of the proximal ends 24 of the optical fibers 18 may vary. For example, an optical connector coupled with the proximal ends 24 may be disposed within the cannula locator device 27 or between the proximal end of the cannula locator device 27 and the camera 26.

In some embodiments, the proximal ends 24 of each of the emitting optical fibers may be coupled with a light emitter (not illustrated in FIG. 2), which may provide the light emitted by the distal ends 20 of the emitting optical fibers.

Referring now to FIG. 3, in some embodiments, a small number of optical fibers 18 may be disposed within the inner lumen 16, which may allow simple, cost-effective detection of a color at the distal tip 12 of the cannula 10. For example, one, two, three, or four optical fibers 18 may be disposed within the inner lumen 16 of the cannula 10. As illustrated in FIG. 3, in some embodiments, an emitting optical fiber 28 and a receiving optical fiber 30 may be disposed within the inner lumen 16. In some embodiments, more than one emitting optical fiber 28 and/or more than one receiving optical fiber 30 may be disposed within the inner lumen.

Referring now to FIG. 4, illustrating another example cannula locator system 31, the proximal ends 24 of the receiving optical fibers 30 of the small number of optical fibers 18 may be coupled with a wavelength detector 32. In some embodiments, the wavelength detector 32 may be configured to receive e reflected light from the proximal ends 24 and detect one or more wavelengths of the reflected light. In some embodiments, the wavelength detector 32 may convert the reflected light or a portion of the reflected light into an electrical signal.

The type of wavelength detector 32 may vary. For example, the wavelength detector 32 may include a prism or diffraction grating and one or more photodiodes. The diffraction grating may split the reflected light into output lights according to wavelength and provide the output lights to the one or more photodiodes, which may convert each of the output lights into an electrical signal. A signal processor 34 coupled with the wavelength detector may receive the electrical signals from the photodiodes and may be configured to determine the color of the reflected light based on the electrical signals.

As another example, the wavelength detector 32 may include a color filter that reflects a portion of the reflected light, which may be received by one or more photodiodes. In some embodiments, the color filter may allow a particular wavelength or band of wavelengths, such as wavelengths corresponding to a color of venous blood or wavelengths corresponding to a color of cerebrospinal fluid, to pass through the color filter. The one or more photodiodes may receive the portion of the reflected light and may be configured to convert the portion into an electrical signal. The signal processor 34 coupled with the wavelength detector 32 may receive the electrical signal from the one or more photodiodes and be configured to determine the color of the reflected light based on the electrical signal. For example, the signal processor 34 may detect an increase in intensity of red light passing through a particular color filter that allows d light to pass, which may indicate the environment of the distal tip 12 includes venous blood and the distal tip 12 is located within the blood vessel.

In some embodiments, the signal processor 34 may determine the color of the reflected light is a particular color, and in response to the determination that the color of the reflected light is a particular color, the signal processor 34 may be further configured to initiate an alarm signal and/or to display the particular color. For example, in response to the determination that the color of the reflected light is red or dark red, which may indicate that the distal tip 12 of the cannula 10 is within the blood vessel of the patient, the signal processor may be configured to initiate an alarm signal, which may include an audible noise, a flashing light, etc. The alarm signal may indicate to a clinician that the distal tip 12 of the cannula 10 is located in a desired environment, such as, for example, within the blood vessel, within the cerebrospinal fluid, etc.

In some embodiments, the proximal ends 24 of each of the emitting optical fibers 28 may be coupled with a light emitter 35, which may provide the light emitted by the distal ends 20 of the emitting optical fibers 28.

Figures 5A, 5B:
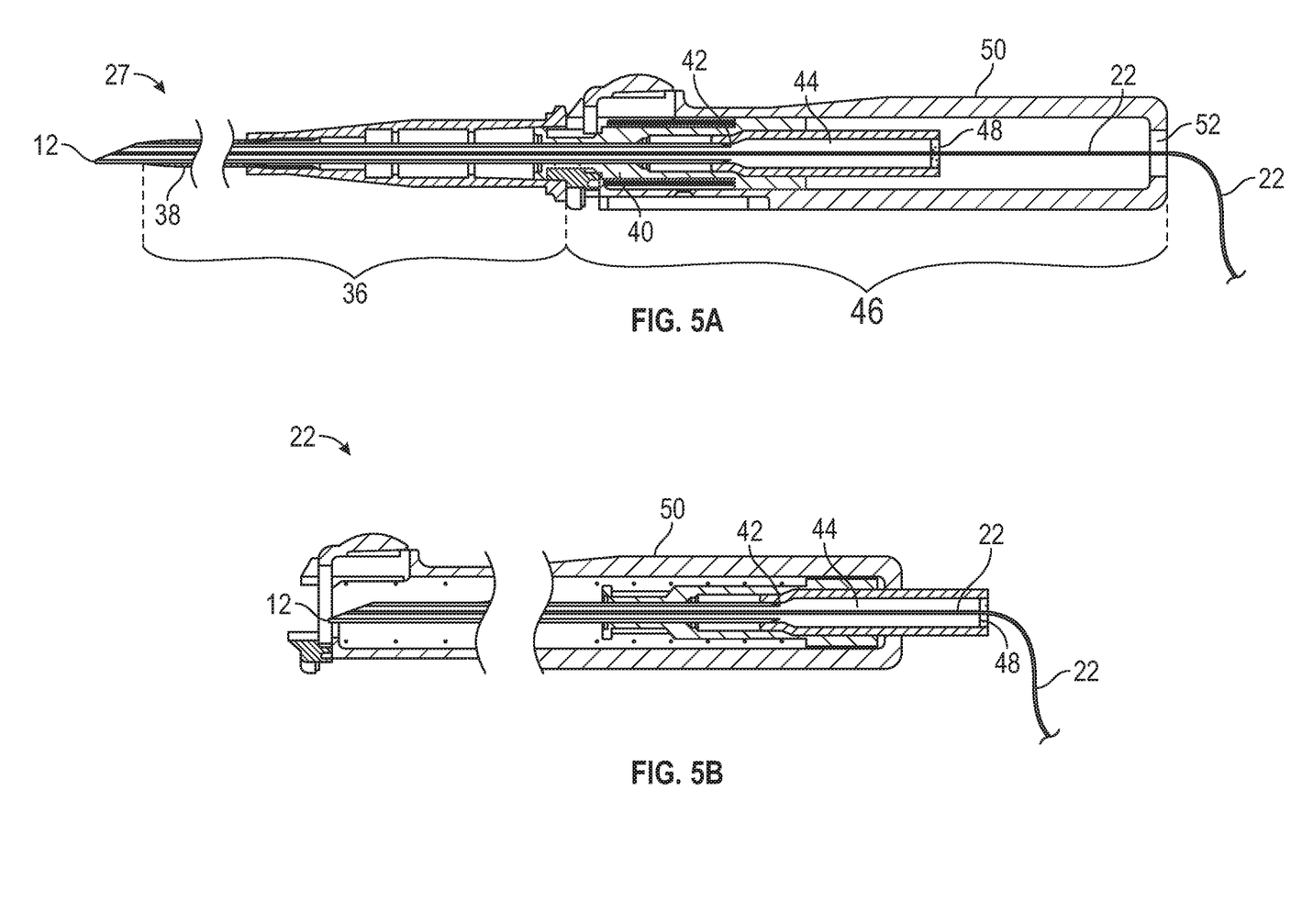
FIG. 5A is a cross-sectional view of the cannula locator device of FIG. 2, according to some embodiments.
FIG. 5B is another cross-sectional view of the cannula locator device of FIG. 2, illustrating the cannula in a shielded position.

Referring now to FIGS. 5A-5B, in some embodiments, the cannula locator device 27 may be an intravenous device, such as, for example, an IV catheter or a PIVC catheter. In some embodiments, the intravenous device may be any intravenous device that includes a cannula. Example intravenous devices may include both straight and ported intravenous catheters such as the AUTOGUARD™ shielded catheter commercially available from Becton, Dickinson, and Company, integrated peripheral intravenous catheters, winged needle sets, blood collection sets, an IV access set such as the BD NEXIVA™ Closed Intravenous (IV) Catheter system available from Becton. Dickinson, and Company, etc. In some embodiments, the optical fibers 18 may extend through the intravenous device from a proximal end of the intravenous device to a distal end of the device or through a portion of the intravenous device. In some embodiments, the optical fibers 18 may exit the distal end of the intravenous device.

In some embodiments, a needle hub of the intravenous device may be configured to move proximally within a needle shield after the catheter is inserted into the patient. In response to the needle hub moving proximally within the needle shield, the cannula and the first and second distal ends of the optical fiber may be retracted into a needle shield of the intravenous device.

In some embodiments, the cannula locator device 27 may include a catheter adapter 36, which may include a catheter 38. In some embodiments, the cannula locator device 27. In some embodiments, the cannula locator device 27 may include a needle hub 40 coupled with a proximal end 42 of the cannula 10. In some embodiments, the needle hub 40 may be selectively coupled with the catheter adapter 36. In some embodiments, the cannula locator device 27 may include a flash chamber 44, which may be coupled with the needle huh 40. In some embodiments, the flash chamber 44 may include a body 46 and an air permeable membrane 48. An internal cavity of the body 46 of the flash chamber 44 may be in fluid communication with the inner lumen 16 of the cannula 10.

In some embodiments, the cannula locator device 27 may include a needle shield 50 within which the flash chamber 44 may be contained. In some embodiments, the optical fibers 18, which may include the sheath 22, may extend through an opening 52 in a proximal end of the needle shield 50. In some embodiments, the needle hub 40 and the flash chamber 44 may be configured to move proximally within the needle shield 50 after the catheter 38 is inserted into the blood vessel of the patient to thereby retract the cannula 10 and the distal ends 20 of the optical fibers 18 into the needle shield 50, as illustrated in FIG. 5B. In some embodiments, the needle shield 50 may be removed the catheter adapter 36, and the optical fibers 18 may be disposed of with the needle shield 50. In some embodiments, the cannula 10 and the optical fibers 18 may be coupled together, which may allow them to move together with respect to the cannula locator device 27.

Figure 6:
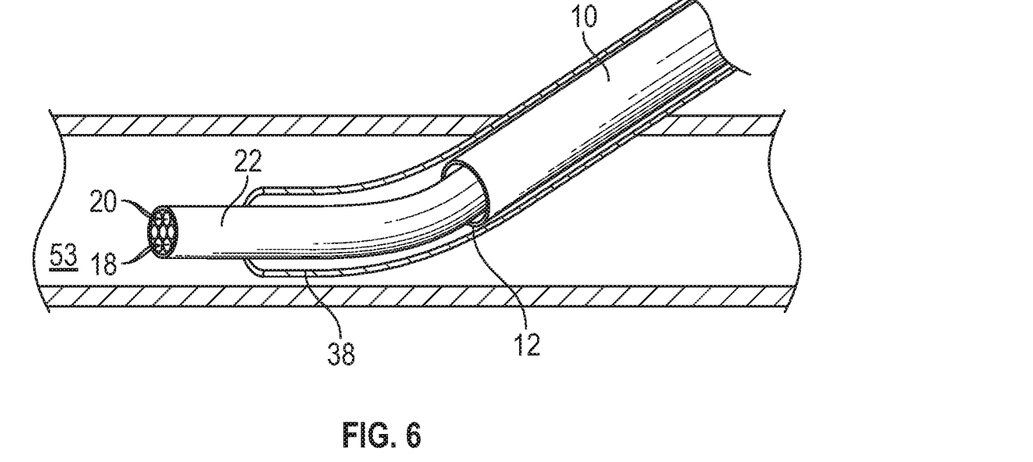
FIG. 6 is a perspective view of example optical fibers configured to act as a guide for placement of a catheter, according to some embodiments.

Referring now to FIG. 6, in some embodiments, the optical fibers 18 may be configured to perform similarly to a guidewire. Typically, a guidewire may be made of metal and used to advance a catheter into the blood vessel of the patient. Typically, an area of the skin may be antiseptically prepared and a local anesthetic may be applied after which a nick is made in the skin over the site of a blood vessel to be catheterized. A cannula is then introduced into the blood vessel and its introduction may be indicated by flash back or back flow of blood to the inner needle and/or a flash chamber. The cannula may then be withdrawn and replaced with a guidewire which is then introduced through the cannula for a distance, for example, six to ten inches. External pressure may then applied to hold the guidewire in place while the cannula is withdrawn after which the guidewire is fed into the blood vessel. Once the guidewire reaches the selected area, the catheter is passed over the guidewire to the selected area after which the guidewire is withdrawn from the catheter.

As described, typically, the catheter may follow the guidewire into the blood vessel to reduce trauma to the blood vessel during advancement of the catheter into the blood vessel. In some embodiments, the optical fibers 18 may be configured to move past the distal tip 12 of the cannula 10 to guide a catheter, such as, for example, catheter 38 illustrated in FIGS. 5A-5B, or any other catheter, into a desired location in the patient, such as, for example, the blood vessel 53. Any number of optical fibers 18 may be used to guide the catheter 38. For example, one, two, three, four, or more optical fibers 18 may be used to guide the catheter 38.

In some embodiments, the optical fibers 18 may not only reduce trauma to the blood vessel 53 by guiding the catheter 38 into the blood vessel 53, but may also illuminate the blood vessel 53, allowing the clinician o more clearly see a location of the blood vessel 53. In some embodiments, the optical fibers 18 that guide the catheter 38 may be included in the cannula locator device 27 in the cannula locator system 23 of FIG. 2 and configured to generate an image of an environment of the distal ends 20 of the optical fibers 18 in a same or similar way as described with respect to the cannula locator device 27 in the cannula locator system 23. In some embodiments, the optical fibers 18 that guide the catheter 38 may be included in the cannula locator device 27 in the cannula locator system 31 of FIG. 4 and configured to detect the color of the environment of the distal ends 20 of the optical fibers 18 in a same or similar way as described with respect to the cannula locator device 27 in the cannula locator system 31.

In some embodiments, the optical fibers 18 may uncoupled from the cannula 10 and/or freely movable within the cannula 10 in a distal and/or proximal direction, which may allow the optical fibers 18 to be advanced past the distal tip 12 of the cannula 10. In some embodiments, a portion of the optical fibers 18 proximal to a proximal end of the cannula locator device 27 may be slack, which may allow the optical fibers 18 to be advanced past the distal tip 12 of the cannula 10. In some embodiments, the air permeable membrane 48 may be configured to allow the optical fibers 18 to slide through the air permeable membrane 48 without allowing blood to leak out of the air permeable membrane 48.

Figure 7:
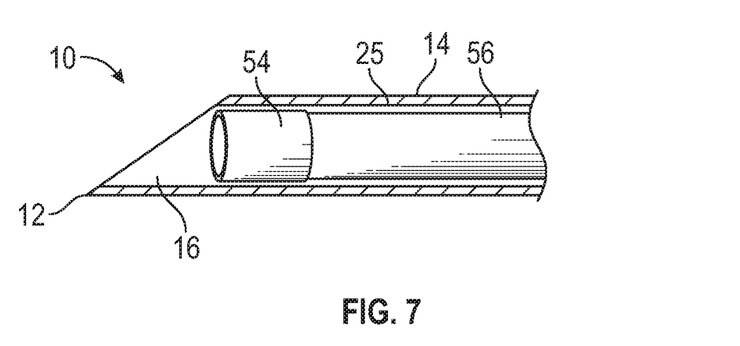
FIG. 7 is a cut-away side view illustrating an example camera disposed within the cannula, according to some embodiments.

Referring now to FIG. 7, in some embodiments, a particular cannula locator device 27 may include a light detector, other than the optical fibers 18, disposed within the inner lumen 16 of the cannula 10. For example, a particular light detector disposed within the inner lumen 16 of the cannula 10 may include a camera 54 coupled with one or more electrical cables enclosed in a sheath 56. In some embodiments, the camera 54 may be disposed at least proximate the distal tip 12 of the cannula 10. In some embodiments, the sheathed electrical cables may extend through the inner lumen 16 of the cannula 10. In some embodiments, the camera 54 may he spaced apart from the inner wall 25 of the elongated tubular shaft 14, which may allow blood to flow into the cannula 10 and through a flash back notch in the cannula 10. In some embodiments, the camera 54 may be configured to generate an image of the environment of the distal tip 12 of the cannula 10 and provide the clinician with a "first person" point of view from a perspective of the distal tip 12.

The cannula locator device 27 may or may not include the flash chamber 44, illustrated in FIGS. 5A and 5B. In some embodiments, the cannula locator device 27 may include the flash back notch. In some embodiments, the flash back notch may define an opening in the elongated tubular shaft 14 and may be configured to allow blood to flow between the distal tip 12 and the flash back notch. In some embodiments, the blood may then flow out of the flash back notch and into a portion of the cannula locator device 27, such as, for example, the catheter 38, to indicate to the clinician that the distal tip 12 has entered the blood vessel.

Figure 8:
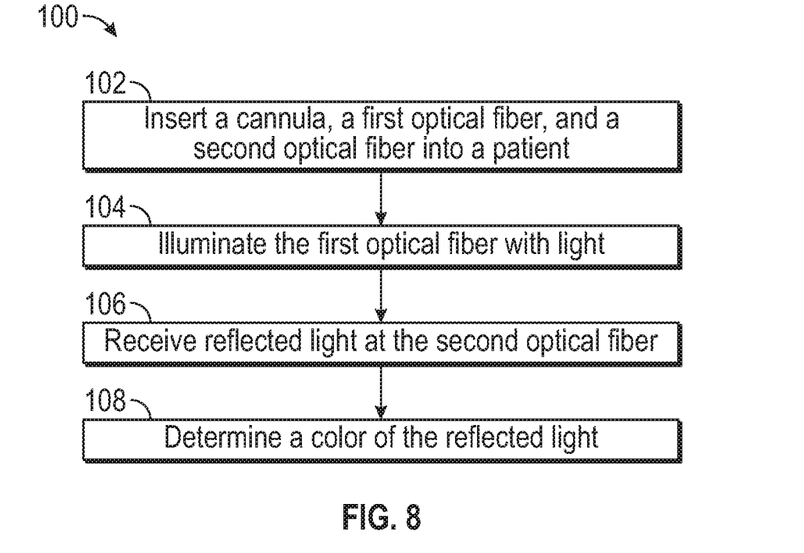
FIG. 8 is a flow diagram of an example method of determining a position of the cannula.

FIG. 8 is a flow diagram of an example method 100 of determining a position of a cannula. The cannula may correspond to the cannula 10 illustrated in FIGS. 1-7. The method may begin at block 102 in which the cannula, a first optical fiber, and a second optical fiber may be inserted into a patient. In some embodiments, the first optical fiber and the second optical fiber may correspond to the optical fibers 18 discussed with respect to FIGS. 1-7. In some embodiments, the first optical fiber may correspond to the emitting optical fiber 28 of FIG. 3 and/or the second optical fiber may correspond to the receiving optical fiber 30 of FIG. 3. In some embodiments, the cannula, the first optical fiber, and/or the second optical fiber may be disposed within the cannula locator system 23 or the cannula locator system 31. In some embodiments, the cannula, the first optical fiber, and/or the second optical fiber may be included in a cannula locator device such as the cannula locator device described in FIGS. 1-7.

In some embodiments, the cannula may include a distal tip, an elongated tubular shaft, and an inner lumen formed by the elongated tubular shaft. In some embodiments, the first and second optical fibers may be disposed within the inner lumen of the cannula. In some embodiments, the first optical fiber may include a first distal end and a first proximal end. In some embodiments, the first optical fiber may be configured to emit light. In some embodiments, the second optical fiber may include a second distal end and a second proximal end. In some embodiments, the second optical fiber may be configured to receive reflected light. Block 102 may be followed by block 104.

At block 104, the first optical fiber may be illuminated with light. In some embodiments, illuminating the first optical fiber with light may be accomplished using a light emitter, which may be coupled to the first proximal end of the first optical fiber. Block 104 may be followed by block 106.

At block 106, the reflected light may be received at the second optical fiber. For example, the light may be reflected from the environment of the distal tip of the cannula and received at the second distal end of the second optical fiber. Block 106 may be followed by block 108.

At block 108, a color of the reflected light may be determined. In some embodiments, the color of the reflected light may be determined using a wavelength detector as described with respect to wavelength detector 32 of FIG. 4, for example. Although illustrated as discrete blocks, various blocks may be divided into additional blocks, combined into fewer blocks, or eliminated, depending on the desired implementation.

In addition to the previously described embodiments of the cannula locator device, the cannula locator device may be modified in any suitable manner that allows it to fulfill its intended purpose. Further, the cannula locator device may be used in any suitable manner. Also, in addition to the previously described embodiments of the cannula locator system, the cannula locator system of which the cannula locator device is a part, may be modified in any suitable manner that allows it to fulfill its intended purpose. By way of non-limiting illustration, the signal processor may be coupled with a display, allowing the clinician to view the image and/or color at the distal tip of the cannula and/or the distal ends of the optical fibers. Also by way of non-limiting illustration, the cannula locator device may include different components and/or variations of the components, such as the catheter adapter, the catheter, the needle hub, the flash chamber, etc. illustrated in FIGS. 5A-5B.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A cannula locator device comprising:
   a catheter adapter having a proximal end and a distal end, the catheter adapter including a catheter that extends from the distal end of the catheter adapter;
   a needle hub having a proximal end and a distal end, the needle hub including a cannula that extends from the distal end of the needle hub, the cannula being positioned within and extending through the catheter adapter and the catheter such that a distal tip of the cannula extends distally beyond a distal end of the catheter;
   a flash chamber coupled to the proximal end of the needle hub, the cannula forming a fluid pathway into the flash chamber;
   a needle shield having a proximal end and a distal end, the distal end of the needle shield being coupled to the proximal end of the catheter adapter, the needle hub and the flash chamber being contained within the needle shield;
   a sheath having a proximal end and a distal end, the distal end of the sheath being positioned adjacent the distal tip of the cannula, the sheath extending proximally through the cannula, the flash chamber and out through the proximal end of the needle shield;
   one or more emitting optical fibers and one or more receiving optical fibers contained within the sheath, a distal end of each of the one or more emitting optical fibers and the one or more receiving optical fibers being positioned at the distal end of the sheath, a proximal end of each of the one or more emitting optical fibers and the one or more receiving optical fibers extending within the sheath through the proximal end of the needle shield;
   a light emitter that is configured to emit light into the proximal end of each of the one or more emitting optical fibers; and
   circuitry that is configured to receive reflected light from the proximal end of each of the one or more receiving optical fibers, the circuitry being configured to process the reflected light to detect when the distal tip of the cannula is within a patient's vasculature.

2. The cannula locator device of claim 1, wherein the proximal end of the flash chamber includes an air permeable membrane, the sheath extending through the air permeable membrane.

3. The cannula locator device of claim 1, wherein the needle hub retracts proximally into the needle shield.

4. The cannula locator device of claim 3, wherein the proximal end of the needle hub extends proximally through the proximal end of the needle shield when the needle hub is retracted proximally into the needle shield.

5. The cannula locator device of claim 3, wherein the distal tip of the cannula and the distal end of the sheath are secured within the needle shield when the needle hub retracts proximally into the needle shield.

6. The cannula locator device of claim 3, wherein the needle shield is detachable from the catheter adapter after the needle hub retracts proximally into the needle shield to thereby separate the cannula and the sheath from the catheter adapter.

7. The cannula locator device of claim 1, wherein the circuity comprises a waveguide detector.

8. The cannula locator device of claim 7, wherein the waveguide detector comprises a prism or diffraction grating and one or more photodiodes.

9. The cannula locator device of claim 7, wherein the circuitry further comprises a signal processor.

10. The cannula locator device of claim 1, wherein the circuitry comprises a camera.

11. The cannula locator device of claim 1, wherein the circuitry detects when the distal tip of the cannula is within a patient's vasculature based on a color of the reflected light.

12. The cannula locator device of claim 1, wherein the circuitry is configured to output an alarm when the circuitry detects that the distal tip of the cannula is within a patient's vasculature.

13. The cannula locator device of claim 1, wherein the sheath and the one or more emitting optical fibers and one or more receiving optical fibers contained within the sheath are configured to move within the cannula to thereby enable the sheath and the one or more emitting optical fibers and one or more receiving optical fibers to be advanced distally beyond the distal tip of the cannula.

14. The cannula locator device of claim 1, wherein the light emitter and the circuitry are located external to the needle shield.

15. A cannula locator device comprising:
    a catheter adapter having a proximal end and a distal end, the catheter adapter including a catheter that extends from the distal end of the catheter adapter;
    a needle hub having a proximal end and a distal end, the needle hub including a cannula that extends from the distal end of the needle hub, the cannula being positioned within and extending through the catheter adapter and the catheter such that a distal tip of the cannula extends distally beyond a distal end of the catheter;
    a flash chamber coupled to the proximal end of the needle hub, the cannula forming a fluid pathway into the flash chamber;
    a needle shield having a proximal end and a distal end, the distal end of the needle shield being coupled to the proximal end of the catheter adapter, the needle hub and the flash chamber being contained within the needle shield;
    a sheath having a proximal end and a distal end, the distal end of the sheath being positioned adjacent the distal tip of the cannula, the sheath extending proximally through the cannula, the flash chamber and out through the proximal end of the needle shield;
    optical fibers contained within the sheath, a distal end of each of the optical fibers being positioned at the distal end of the sheath, a proximal end of each of the optical fibers extending within the sheath through the proximal end of the needle shield;
    a light emitter that is configured to emit light into the proximal end of one or more of the optical fibers; and
    circuitry that is configured to receive reflected light from the proximal end of one or more of the optical fibers, the circuitry being configured to process the reflected light to detect when the distal tip of the cannula is within a patient's vasculature.

16. The cannula locator device of claim 15, wherein the proximal end of the flash chamber includes an air permeable membrane, the sheath extending through the air permeable membrane.

17. The cannula locator device of claim 15, wherein the needle shield is detachable from the catheter adapter after the needle hub retracts proximally into the needle shield to thereby separate the cannula and the sheath from the catheter adapter.

18. The cannula locator device of claim 15, wherein the sheath and the optical fibers contained within the sheath are configured to move within the cannula to thereby enable the sheath and the one or more optical fibers to be advanced distally beyond the distal tip of the cannula.

19. A cannula locator device comprising:
- a catheter adapter having a proximal end and a distal end, the catheter adapter including a catheter that extends from the distal end of the catheter adapter;
- a needle hub having a proximal end and a distal end, the needle hub including a cannula that extends from the distal end of the needle hub, the cannula being positioned within and extending through the catheter adapter and the catheter such that a distal tip of the cannula extends distally beyond a distal end of the catheter;
- a flash chamber coupled to the proximal end of the needle hub, the cannula forming a fluid pathway into the flash chamber;
- a needle shield having a proximal end and a distal end, the distal end of the needle shield being coupled to the proximal end of the catheter adapter, the needle hub and the flash chamber being contained within the needle shield;
- a sheath having a proximal end and a distal end, the distal end of the sheath being positioned adjacent the distal tip of the cannula, the sheath extending proximally through the cannula, the flash chamber and out through the proximal end of the needle shield;
- one or more emitting optical fibers and one or more receiving optical fibers contained within the sheath, a distal end of each of the one or more emitting optical fibers and the one or more receiving optical fibers being positioned at the distal end of the sheath, a proximal end of each of the one or more emitting optical fibers and the one or more receiving optical fibers extending within the sheath through the proximal end of the needle shield;
- a light emitter that is configured to emit light into the proximal end of each of the one or more emitting optical fibers; and
- circuitry that is configured to receive reflected light from the proximal end of each of the one or more receiving optical fibers, the circuitry being configured to process the reflected light to detect when the distal tip of the cannula is within a patient's vasculature;
- wherein the sheath and the optical fibers contained within the sheath are configured to move within the cannula to thereby enable the sheath and the one or more optical fibers to be advanced distally beyond the distal tip of the cannula; and
- wherein the needle hub retracts proximally into the needle shield, the needle shield being detachable from the catheter adapter after the needle hub retracts proximally into the needle shield to thereby separate the cannula and the sheath from the catheter adapter.

20. The cannula locator device of claim 19, wherein the circuitry detects when the distal tip of the cannula is within a patient's vasculature based on a color of the reflected light.

* * * * *